(12) United States Patent
Bardani

(10) Patent No.: US 8,367,103 B2
(45) Date of Patent: Feb. 5, 2013

(54) ORAL TESTOSTERONE COMPOSITION

(76) Inventor: Frank M. Bardani, Purchase, NY (US)

( * ) Notice: Subject to any disclaimer, the term of this patent is extended or adjusted under 35 U.S.C. 154(b) by 186 days.

(21) Appl. No.: 12/924,412

(22) Filed: Sep. 27, 2010

(65) Prior Publication Data

US 2012/0076855 A1 Mar. 29, 2012

(51) Int. Cl.
*A61F 2/00* (2006.01)

(52) U.S. Cl. ...................................... 424/452

(58) Field of Classification Search ........................ None
See application file for complete search history.

(56) References Cited

U.S. PATENT DOCUMENTS 7,138,389 B2 * 11/2006 Amory et al. ................. 514/171
2003/0232097 A1 * 12/2003 Radhakrishnan et al. .... 424/731

* cited by examiner

*Primary Examiner* — Brian Gulledge
*Assistant Examiner* — Snigdha Maewall
(74) *Attorney, Agent, or Firm* — Morton S. Simon, Esq.

(57) ABSTRACT

The composition for oral administration of testosterone to a man who has androgen deficiency and exhibits one or more symptoms of androgen deficiency, comprises testosterone and a mixture of soybean oil and ethanol. Preferably, a pharmaceutically acceptable preservative, such as benzyl alcohol, is included in the composition. The mixture of soybean oil and ethanol is present in the composition in an amount such that when the composition is orally ingested by the testosterone is absorbed and one or more of the symptoms of androgen deficiency is ameliorated. The composition is charged into hard or soft gelatin capsules to produce orally administrable unit dosage forms.

5 Claims, 6 Drawing Sheets

ORAL TESTOSTERONE COMPOSITION

FIELD OF THE INVENTION

This invention is directed to an androgen containing composition, more particularly, a testosterone containing composition for oral use. The composition contains a mixture of soybean oil and ethanol as testosterone absorption promoting agents. Preferably, the composition also contains a preservative such as benzyl alcohol. Unit doses of the composition can be orally administered in hard or soft gelatin capsules.

BACKGROUND OF THE INVENTION

Testosterone decline in men has been well studied in the prior art and is associated with decline in both physical and mental function.

Symptoms of androgen/testosterone deficiency include: reduced libido, hot flushes and sweating, breast development, lethargy and fatigue, depression, reduced muscle mass and strength, increased body fat—particularly around the abdomen and reduced bone mass, loss of body hair, increase in blood low density lipoproteins together with a decrease in high density lipoproteins The most reported symptoms of androgen deficiency are lack of energy, lack of motivation, and reduced libido.

Testosterone replacement has been successfully employed to try and reverse symptoms of androgen/testosterone deficiency.

FDA approved products for testosterone replacement include: topical gels, patches, intramuscular injections of testosterone esters and subcutaneous pellets.

Oral preparations of synthetic androgens have also been used in the prior art but have been associated with significant side effects. Consequently, their usefulness has been very limited.

It is known in the art that free unesterified testosterone is readily absorbed from the gut but is inactivated by the liver before the testosterone reaches the target organs. Only extremely high doses (e.g. 200 mg) have been shown to be measurable in serum.

Testosterone USP is not effective when taken orally by patients in need of such therapy. Consequently, testosterone is generally administered by injection.

Since oral dosage forms are easier to take and use of same affords greater patient compliance, there is a great need in the medical arts for an oral dosage form of testosterone USP which when orally administered provides therapeutically effective blood levels of testosterone.

SUMMARY OF THE INVENTION

The present inventor has surprisingly and unexpectedly found that when a water-insoluble drug, such as testosterone USP, is dissolved in a mixture a soybean oil and ethanol, preferably with a preservative amount of a pharmaceutically acceptable preservative, such as benzyl alcohol USP, and the resultant solution is charged into hard or soft gelatin capsules and orally administered to a man who has androgen deficiency and who exhibits symptoms of androgen deficiency, pharmaceutically effective blood levels of the dosed drug are obtainable and one or more of such symptoms can be ameliorated.

This is surprising and unexpected since when like formulations, except that the soybean oil was replaced by canola oil, corn oil, olive oil or sesame oil, were orally administered to a man who is androgen deficient and who exhibits symptoms of androgen deficiency, the formulations did not afford therapeutically effective blood levels of the dosed drug and failed to ameliorate such symptoms.

Other purposes and advantages of this invention will become apparent from a study of the following portion of the specification, the claims and the attached drawings.

DETAILED DESCRIPTION OF THE INVENTION

Figure 1:
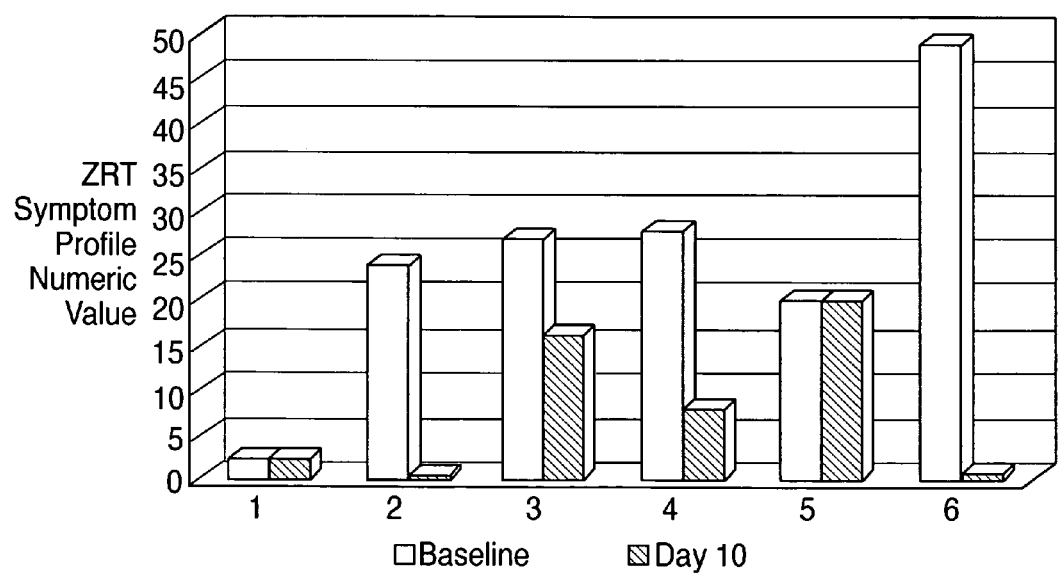
FIG. 1 is a bar graph showing, for each of test subjects 1-6, the system profile numeric value for symptoms of androgen deficiency, at baseline and at day 10 of the treatment.

The oral composition of the present invention comprises:
testosterone, in an amount which when orally administered to man having androgen deficiency and symptoms of androgen deficiency, is sufficient to alleviate a symptom of androgen deficiency in such man;
an amount of a mixture of soybean oil and ethanol, sufficient to enable absorption of the testosterone when the composition is orally administered to said man so that the symptom of androgen deficiency is alleviated;
the ethanol preferably being present in an amount of from about 2.5% to about 10% by weight, based on the total weight of the composition, most preferably about 5% by weight, based on the total weight of the composition;
the soybean oil being present in an amount of from about 70% by weight to about 95% by weight based on the total weight of the composition, preferably from about 75% by weight to about 90% by weight based on the total weight of the composition, more preferably from about 80% to about 90% by weight based on the total weight of the composition, most preferably from about 85% to about 90% by weight based on the total weight of the composition;
and
from 0 to about 10% by weight based on the total weight of the composition, of a pharmaceutically acceptable preservative, preferably benzyl alcohol, more preferably benzyl alcohol in an amount of from about 4% to about 6% by weight based on the total weight of the composition, most preferably benzyl alcohol in an amount of about 5% by weight based on the total weight of the composition.

The following examples are offered for the purpose of illustrating the present invention and are not intended to limit the scope of the invention in any respect.

Example 1

Testosterone Composition

|  | 1 Capsule | 1000 Capsules |
|---|---|---|
| Testosterone USP | 10 mg | 10 Gm |
| Ethanol USP | 15 mg | 15 Gm |
| Soybean Oil USP | 275 mg | 275 Gm |
| Benzyl Alcohol USP | 15 mg | 15 Gm |

Example 2

General Procedure

The composition of the present invention is prepared in accordance with the following general procedure:

The formulation amounts of testosterone and soybean oil are mixed and heated at a temperature of about 140° F. The formulation amount of the ethanol is added to the heated mixture of the testosterone and soybean oil, under agitation. The composition so produced is allowed to cool to a temperature of about 120° F. then the formulation amount of the benzyl alcohol is added thereto and the resultant composition is mixed until a clear solution is obtained. When the solution cools to a temperature of about 100° F. it is charged into gelatin capsules so that each unit dose capsule contains 10 mg testosterone USP, 15 mg ethanol USP, 275 mg Soybean oil USP and 15 mg benzyl alcohol USP.

Example 3

The following study was carried out to determine whether the composition of the present invention, as exemplified by Example 1, is pharmaceutically active in a man who is androgen deficient and has symptoms of androgen deficiency.

A 42 year old male test subject with symptoms of androgen deficiency and previously documented low testosterone levels was orally dosed twice daily with a unit dose capsule containing the testosterone composition of Example 1.

The first oral dose was administered at 8 am on an empty stomach. The second oral dose was administrated at 6 pm with a high fat meal.

Capillary and venous bloodspot levels and salivary hormone levels were measured at two hour intervals during the period that the test subject was awake.

The test subject reported a clinical response to the orally administered test composition and, other than an acne lesion (which cleared without medication), there were no side effects.

Absorption of testosterone was documented on all three of the testing modalities. Capillary bloodspot and saliva showed clear increases in bio-available testosterone.

Because absorption was documented and also correlated with relief of the test subject's symptoms of androgen deficiency, the study of Example 4 was conducted.

Example 4

The absorption of the 10 mg testosterone composition of Example 1, orally administered twice daily, was evaluated in six male test subjects (ages 42, 42. 52, 60, 62 and 77).

Absorption was determined by three different methods.
1. Serum testosterone level was measured at baseline and on days 8, 9 and 10 of treatment.
2. Tissue testosterone (end organ response) was measured by capillary bloodspot, at baseline and on day 10 of treatment.
3. Serum Luteinizing Hormone ("LH") was measured at baseline and on day 10 of treatment.

A suppression of Luteinizing Hormone may reflect adequacy of testosterone therapy.

Estradiol levels were also evaluated.

Description of the Methods Employed

Determination of LH

The ADVIA Centaur LH assay was employed. It is a two-site sandwich immunoassay using direct chemiluminometric technology that employs constant amounts of two antibodies that have specificity for the beta subunit of the intact LH molecule. The first antibody is a monoclonal mouse anti-LH antibody labeled with acridinium ester. The second antibody, in the Solid Phase, is a monoclonal mouse anti-LH antibody that is covalently coupled to paramagnetic particles.

Determination of Estradiol (Ultrasensitive)

The ADVIA Centaur Estradiol-6 III assay is a competitive immunoassay that uses direct chemiluminescent technology. It derives its name from the coupling of the estradiol immunogen at the specificity-enhancing sixth position, allowing for the production of a highly specific antibody. This $17\beta$-estradiol-6-antibody allows the ADVIA Centaur Estradiol-6 III assay to be used across a wide range of applications. Estradiol in a test subject's sample competes with acridinium ester-labeled estradiol for a limited amount of rabbit anti-estradiol antibody. Rabbit anti-estradiol is captured by mouse anti-rabbit IgG, which is coupled to paramagnetic particles.

Determination of Testosterone

Serum testosterone is preformed using standard liquid chromatography-tandem mass spectrometry ("LC-MS")

Capillary Blood Spot Testing®

Testosterone is determined by finger-prick analysis preformed as close to serum testing as possible. The testosterone in the blood spot assay represents the level in whole blood (includes all blood cells that also carry hormones to target tissues). As supplemented fat-soluble hormones may disappear from serum more rapidly, capillary blood spot may more accurately reflect response to therapy.

The capillary blood spot testosterone assay is carried out by extracting the blood spots in methanol, drying the extracts over nitrogen then reconstituting them in assay buffer. Blood spot standards and controls (Bio-Rad) are prepared by combining with washed red blood cells 50-50 and drying on filter paper. Standards and controls are prepared in parallel with clinical samples. Other controls are prepared with whole blood collected by venipuncture. Half are prepared as serum and the other half are prepared as blood spots. R values are determined from the venipuncture serum/blood spot tests. Assays are preformed using the ELISA method ("Enzyme-Linked Immunosorbent Assay").

ZRT System Profile

The ZRT system profile (ZRT Laboratory, Beaverton, Oreg.) used to evaluate the results is intended as a disease-specific quality of life instrument.

Symptoms of hormonal imbalance (e.g. hot flashes, sleep disturbances, etc. [50 total symptoms]) were self-graded by the test subjects as none (0), mild (1), moderate (2) or severe (3). These symptoms are measurable and correlate with specific hormone deficiencies.

The system profile employed is based on specific symptoms of estrogen and androgen deficiencies. It is scored, for each symptom, by multiplying relative frequency of the symptom (a constant value rated from 0-100%) times the test subject's self-rated intensity of the symptom (o=none, 1=mild, 2=moderate and 3=severe).

The frequency, which is constant, is multiplied by the test subject's self-rated severity of the symptom to derive a score for the symptom of from 0 to 300.

Each of the individual symptom scores for estrogen deficiency or androgen deficiency is added to derive a total score. This total score is then divided by the highest score possible for the symptom category (e.g. estrogen deficiency) to derive a percent (0-100%) with 100% representing all symptoms within a symptom category scoring 3 (=severe).

The advantage of this method is that it allows some appreciation for relative individual changes in individual symptoms as well as symptom categories of hormone deficiency or excess. Any relative changes or improvement due to hormone therapy would be reflected in the individual symptoms and a reduction in the percentage of the overall symptom profile.

Referring now to the results with respect to the relief of symptoms of andropause, as illustrated in FIG. 1 hereof. FIG. 1 graphs numeric values for symptoms of androgen deficiency, for each of the six test subjects. A decline is indicative of improvement in symptoms.

It is evident from the graph data that with oral therapy with the composition of Example I four of the six test subjects had significant relief of symptoms related to androgen deficiency. Test subject 1 had very few symptoms to start with. Test subject 5 reported that he noticed no difference, despite, as seen in FIG. 2, showing excellent absorption on both serum and capillary blood spot testing.

Figure 2:
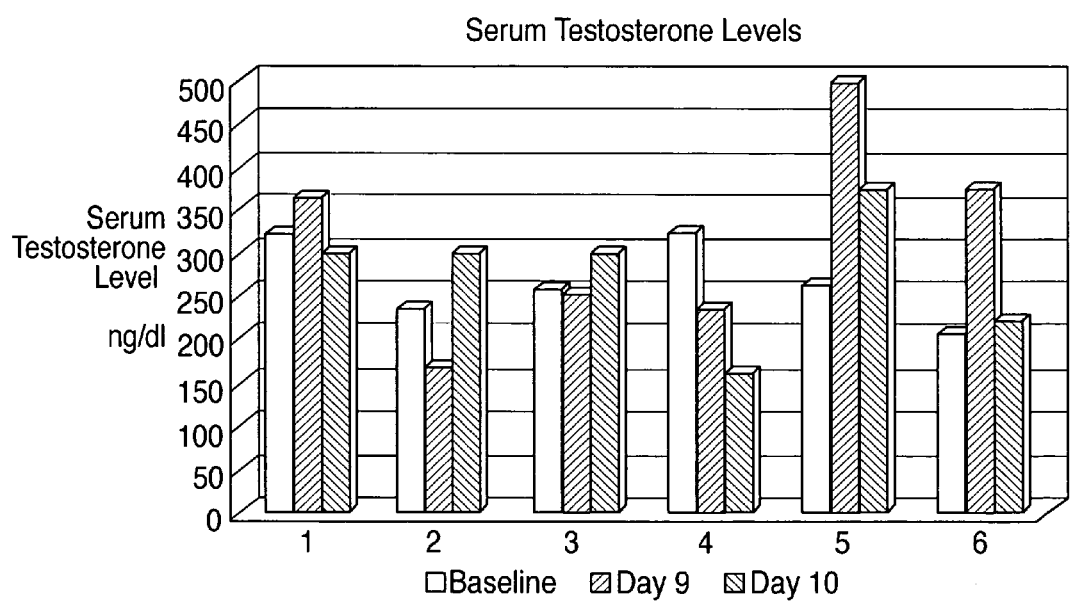
FIG. 2 is a bar graph showing, for each of test subjects 1-6 on the twice a day regimen of the 10 mg oral testosterone capsule composition of Example 1, the serum testosterone level at baseline, at days 9 and 10 of the treatment.

Turning now to FIG. 2, which graphs serum testosterone levels obtained with twice daily oral dosing with the 10 mg testosterone capsule composition of Example I. As is seen from the depicted results, serum testosterone levels were successfully measured at baseline and on days 9 and 10 of treatment. Overall, there was a minimal increase in serum testosterone levels over baseline.

Mean serum testosterone level on day 1 was 267 ng/dl. On day 9 of treatment, mean serum testosterone level was 313 ng/dl. On day 10 of treatment, mean serum testosterone level was 274 ng/dl.

Only test subject 4 showed a decline in measured testosterone in serum, on days 9 and 10 of treatment. However, this test subject showed a relief in androgen deficiency symptoms and an increase in capillary testosterone levels with therapy.

This may be due to the fact that hormones are fat-soluble and leave the serum quickly after supplementation.

Figure 3:
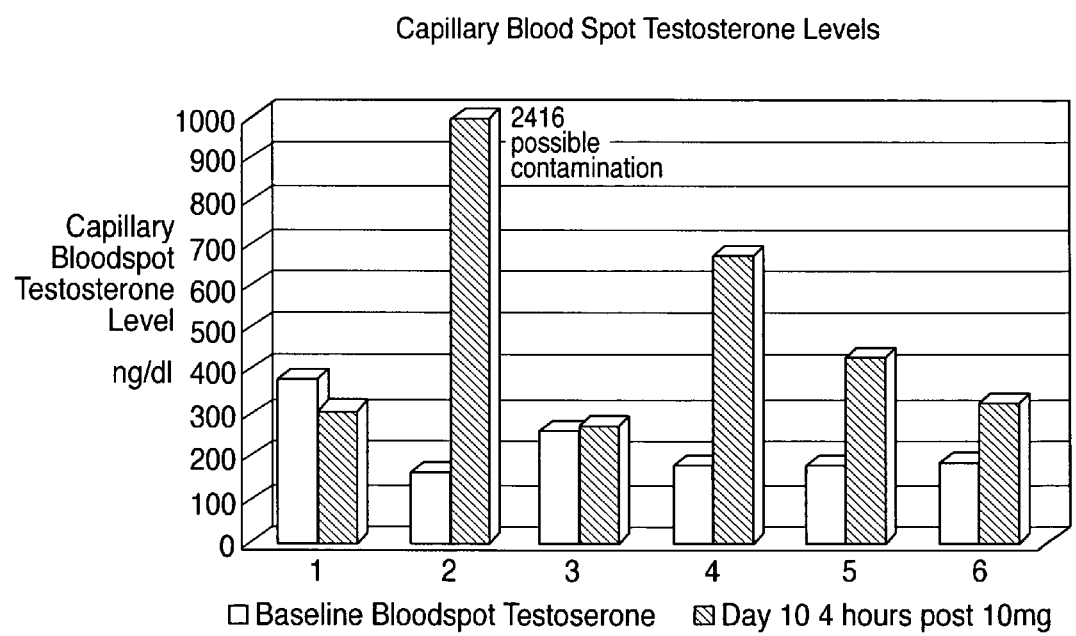
FIG. 3 is a bar graph showing, for each of test subjects 1-6 on the twice a day regimen of the 10 mg oral testosterone capsule composition of Example 1, the capillary bloodspot testosterone level at baseline and at day 10 of the treatment (four hours after oral administration of the 10 mg oral testosterone capsule composition of Example 1)

Attention is now directed to the results of FIG. 3, which graphically illustrates capillary blood spot testosterone levels at baseline and at day 10 after a course of treatment with twice daily oral administration of the composition of Example I.

As seen from the results, capillary blood spot testing, which better reflects tissue levels, showed a significant increase in levels in four of the six test subjects. Test subject 2 had such high levels (2416 ng/dl) that it was felt he may have had contamination due to exposure at work. His venous levels were minimally elevated on day 10 of treatment and all of his symptoms of testosterone deficiency resolved on therapy.

Mean capillary blood spot testosterone levels at baseline were 233 ng/dl, which increased to over 500 (if one includes the 1000 ng/dl of test subject 2) or to 410 (if one excludes the test result of test subject 2).

Figure 4:
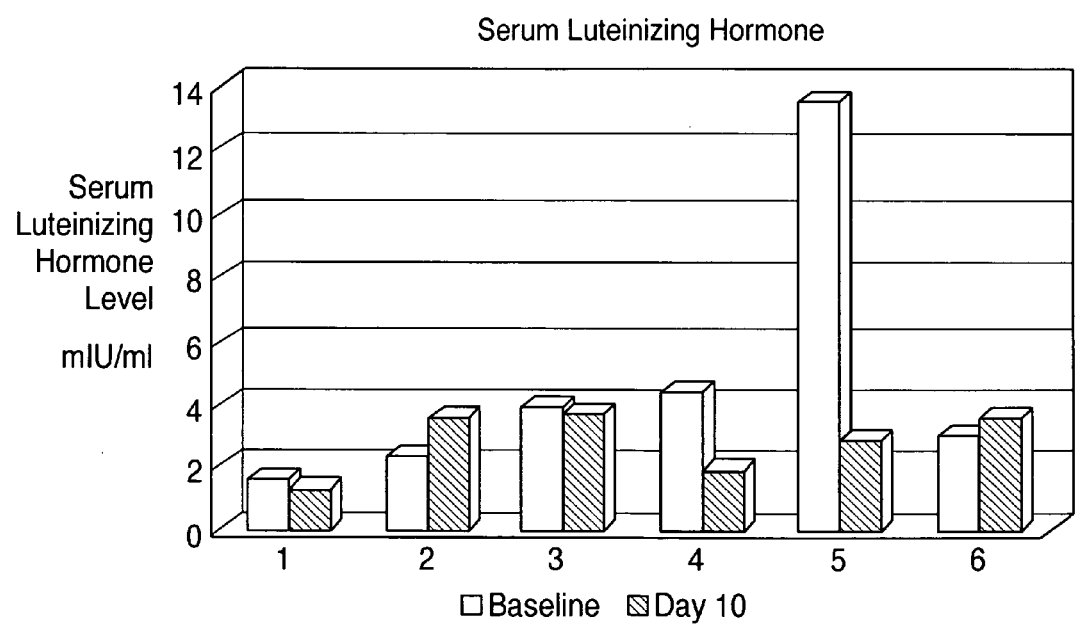
FIG. 4 is a bar graph showing, for each of test subjects 1-6 on the regimen of the 10 mg oral testosterone capsule composition of Example 1, the serum luteinizing hormone level at baseline and at day 10 of the treatment.

FIG. 4 graphically depicts the serum luteinizing hormone test results, at baseline and at day 10 of treatment, for each of the six test subjects.

Testosterone inhibits Luteinizing Hormone ("LH") secretion by acting directly on the anterior pituitary and by inhibiting the secretion of Gonadotropin-releasing Hormone (GnRH) from the hypothalamus.

The single test subject 5 (age 42) who had a Serum Luteinizing Hormone level of over 11 mIU/ml showed a significant decline with oral testosterone therapy with the composition of Example 1. A second test subject 4 with an LH level over 4 mIU/ml, also showed a decline with the oral administration of the testosterone composition of Example I.

Figure 5:
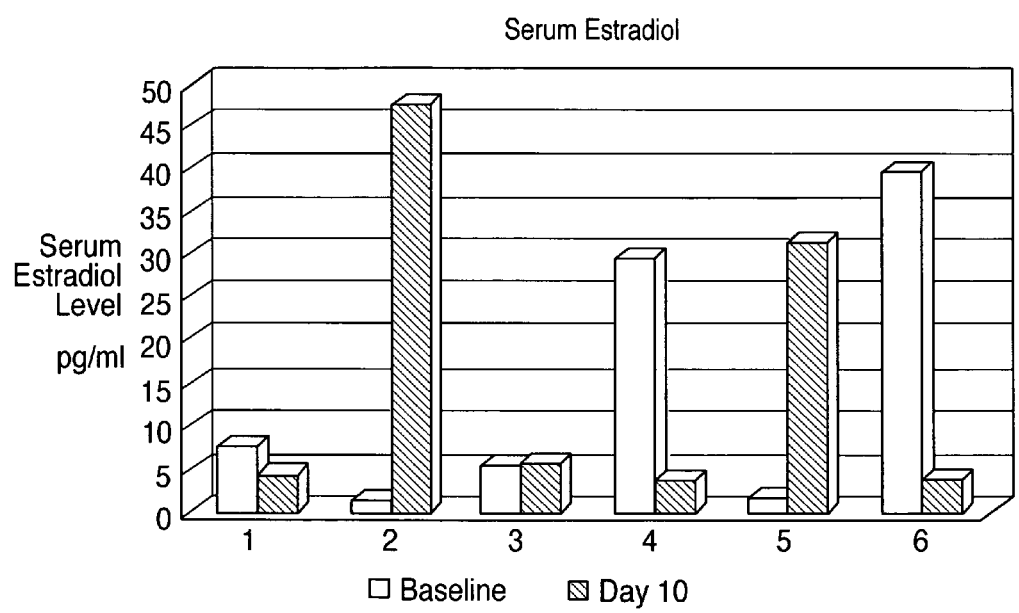
FIG. 5 is a bar graph showing, for each of test subjects 1-6 on the regimen of the 10 mg oral testosterone capsule composition of Example 1, the serum estradiol level at baseline and at day 10 of the treatment.

FIG. 5 graphically depicts the serum estradiol levels, at baseline and at day 10, for each of the six test subjects treated with the oral testosterone composition of Example 1.

As is seen from the graphically depicted test results, ultrasensitive serum estradiol rose in two of the test subjects, declined in three, and remained unchanged in one. Mean Estradiol went from 14.6 to 16.5 pg/ml. A single serum estradiol may be misleading. Test subject 2 could have been exposed to estradiol.

Figure 6:
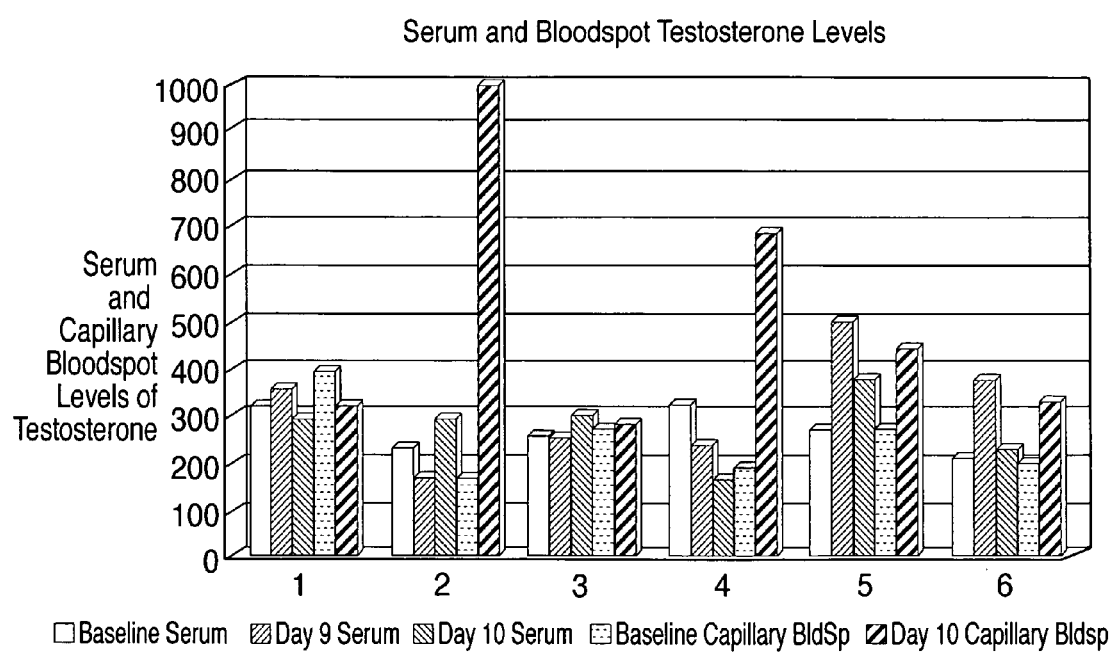
FIG. 6 is a bar graph showing, for each of test subjects 1-6 on the regimen of the 10 mg oral testosterone capsule composition of Example 1, the serum level and the bloodspot testosterone level at baseline and at days 9 and 10 of the treatment.

FIG. 6 graphically compares the serum and capillary blood spot testosterone levels of the six test subjects treated with the oral testosterone composition of Example 1, at baseline and at days 9 and 10 of treatment.

The results graphically illustrated in FIGS. 1-6 demonstrate that testosterone is absorbed when the composition of the present invention is orally administered. More importantly, oral administration of the composition of the present invention was able to relieve symptoms of testosterone deficiency in the majority of test subjects.

It should be appreciated that the soybean oil is a critical component of the composition of the present invention.

Other oils were evaluated as a possible replacement for soybean oil in the composition of the instant invention.

Compositions of Example 1 were prepared only the formulation amount of the soybean oil in the composition was respectively replaced by canola oil, corn oil, olive oil and sesame oil.

Surprisingly and unexpectedly, when such compositions were orally administered to an androgen deficient man having symptoms of androgen deficiency the symptoms were not ameliorated. This indicates that the testosterone in such compositions was not absorbed or the amount absorbed was insufficient to exert an androgen deficiency symptom ameliorating effect.

The present invention includes within its ambit the method for producing an oral dosage form of testosterone, preferably a hard gelatin capsule or soft gelatin capsule that contains the composition of the present invention.

The method comprises incorporating in the oral dosage form testosterone and an amount of a mixture of soybean oil and ethanol that, when the dosage form is administered to a man who has androgen deficiency and exhibits symptoms of androgen deficiency, is sufficient to increase oral absorption of the testosterone so that one or more of such symptoms is ameliorated.

Optionally, a pharmaceutically acceptable preservative is incorporated in the oral dosage form in an amount sufficient to preserve the composition. Preferably, the preservative is benzyl alcohol.

What is claimed is:

1. A composition for oral administration of testosterone to a man having androgen deficiency and exhibiting one or more symptoms of androgen deficiency, said composition consisting of testosterone, ethanol, soybean oil and, optionally, benzyl alcohol, the ethanol being present in an amount of from about 2.5% to about 10% by weight based on the total weight of the composition, the benzyl alcohol being present in an amount of from 0 to about 10% by weight based on the total weight of the composition, the soybean oil being present in an amount of from 70% to about 95% by weight based on the total weight of the composition, the testosterone being present in an amount which in the absence of the ethanol and soybean oil would not be effective to ameliorate said one or more of symptoms when the composition is orally administered to said man but which in the presence of the ethanol and soybean oil is absorbed and is effective to ameliorate said one or more symptoms.

2. A gelatin capsule unit dosage form of the composition as claimed in claim 1, the composition being encased within the gelatin capsule and containing 10 mg testosterone, 15 mg ethanol, 275 mg soybean oil and 15 mg benzyl alcohol.

3. A composition, in unit dosage form, for oral administration of testosterone to a man having androgen deficiency and exhibiting one or more symptoms of androgen deficiency, said composition consisting of 10 mg testosterone, 275 mg soybean oil, 15 mg ethanol and 15 mg benzyl alcohol; the amount of benzyl alcohol being sufficient to preserve the composition; the amount of soybean oil and ethanol present in the composition enabling the testosterone to be absorbed when the composition is orally ingested by said man so that one or more of said symptoms is ameliorated.

4. The composition, as claimed in claim 3, wherein the unit dosage form is a hard or soft gelatin capsule.

5. Process for producing an oral dosage form, as claimed in claim 4, comprising heating testosterone and soybean oil at a temperature of about 140° F. to produce a first composition; adding ethanol to the first composition under agitation whereby a second composition is produced; cooling the second composition to a temperature of about 120° F.; adding benzyl alcohol to the cooled second composition and mixing until a clear solution is obtained and, when the clear solution cools to a temperature of about 100° F., charging it into gelatin capsules so that each charged capsule contains 10 mg testosterone, 15 mg ethanol, 275 mg soybean oil and 15 mg benzyl alcohol.

\* \* \* \* \*